United States Patent [19]

Takagawa et al.

[11] Patent Number: 5,254,769
[45] Date of Patent: Oct. 19, 1993

[54] METHOD OF ISOMERIZATION OF DIMETHYLNAPHTHALENES

[75] Inventors: Makoto Takagawa; Ken Yamagishi; Kazuo Nagagata, all of Tsukuba, Japan

[73] Assignee: Mitsubishi Gas Chemical Company, Inc., Tokyo, Japan

[21] Appl. No.: 851,827

[22] Filed: Mar. 16, 1992

[30] Foreign Application Priority Data

Jun. 21, 1991 [JP] Japan .................................. 3-177648
Oct. 23, 1991 [JP] Japan .................................. 3-304104

[51] Int. Cl.$^5$ .............................................. C07C 5/22
[52] U.S. Cl. .................................... 585/477; 585/478; 585/479; 502/224
[58] Field of Search ............... 585/477, 734, 747, 478, 585/479; 502/224

[56] References Cited

U.S. PATENT DOCUMENTS 2,527,825 10/1950 Kemp ................................... 585/477
3,109,036 10/1963 Suld et al. ............................ 585/477

FOREIGN PATENT DOCUMENTS 47-50622 12/1972 Japan .
48-76852 10/1973 Japan .
49-134634 12/1974 Japan .
50-89353  7/1975 Japan .
58-4008   1/1983 Japan .
59-88433  5/1984 Japan .

Primary Examiner—Asok Pal
Assistant Examiner—P. Achutamurthy
Attorney, Agent, or Firm—Frishauf, Holtz, Goodman & Woodward

[57] ABSTRACT

Dimethylnaphthalenes are isomerized into 2,6-dimethylnaphthalene by utilizing hydrogen fluoride as a catalyst and straight chain saturated aliphatic hydrocarbons having carbon atoms in the range from 5 to 12 as the solvent. Isomerization to other undesirable isomers such as 2,7-dimethylnaphthalene and side reactions such as disproportionation are suppressed and a very high degree of the isomerization to 2,6-DMN can be attained.

17 Claims, No Drawings

METHOD OF ISOMERIZATION OF DIMETHYLNAPHTHALENES

BACKGROUND OF THE INVENTION

1. Field of the Invention

The present invention relates to a novel method of isomerization of dimethylnaphthalenes. More particularly, the present invention relates to a novel method of isomerization of dimethylnaphthalenes which are utilized for the preparation of 2,6-dimethylnaphthalene which is, in turn, useful as the material for the preparation of 2,6-naphthalenedicarboxylic acid.

2,6-Naphthalenedicarboxylic acid has important industrial application as a raw material for high performance polyester, such as polyethylene naphthalate. Fibers and films made of polyethylene naphthalate have excellent tensile strength and heat resistance.

2. Description of the Prior Art 2,6-Dimethylnaphthalene is the material utilized for the preparation of 2,6-naphthalenedicarboxylic acid and a high degree of purity is required. (Dimethylnaphthalene will be abbreviated as DMN in the following descriptions.)

In DMN, there are 10 isomers having the two methyl groups at different positions in the molecule. It is required that 2,6-DMN comprising substantially no other isomers be prepared in large quantities with a reasonably economical efficiency.

In the isomerization of DMN, it has been known that neither the isomerization between the adjacent $\beta$-positions nor the isomerization by the transfer of a methyl group on one ring to the other takes place more easily than the isomerization between an $\alpha$-position and its adjacent $\beta$-position. Thus, with respect to the isomerization, DMN can be classified into the following four groups. The isomerization between the following different groups takes place less readily than that within the same group.

A group: 1,5-DMN, 1,6-DMN, 2,6-DMN
B group: 1,8-DMN, 1,7-DMN, 2,7-DMN
C group: 1,4-DMN, 1,3-DMN, 2,3-DMN
D group: 1,2-DMN 2,6-DMN can be prepared by a method of isomerization and isolation after the methylation of methylnaphthalene or naphthalene or by a method of the isolation of 2,6-DMN from tar fractions or petroleum fractions. The fractions or the reaction products contain almost all of the isomers of the four groups and isomerization between the isomers of the different groups is necessary for the efficient preparation of 2,6-DMN from such kind of fraction or reaction products. As a method of isomerization between the isomers of the different groups, for example, a method utilizing a specific zeolite is described in Japanese Laid-open Patent Publication Showa 59-88433. However, the method requires high temperatures for the isomerization and side reactions other than the desired isomerization, such as disproportionation, takes place to a large degree, leading to low yields of the desired 2,6-isomer.

When a mixture of various DMN isomers is isomerized to prepare the 2,6-isomer, the mixture inevitably contains many isomers which are difficult to isomerize to the 2,6-isomer. The yield of 2,6-isomer is low and the isolation of the desired isomer from many other isomers is necessary. Thus, the preparation of the 2,6-isomer in such cases is not efficient.

Another example of the conventional methods for the preparation of DMN is as follows. A method for preparing o-tolylpentene-2 by the reaction of o-xylene and butadiene in a high yield is described in Japanese Laid-open Patent Publication Showa 49-134634. A method for preparing 1,5-dimethyltetraline by the cyclization of o-tolylpentene-2 is described in Japanese Laid-open Patent Publication Showa 50-89353. A method for preparing 1,5-DMN in a high yield and in a high selectivity by the dehydrogenation of 1,5-dimethyltetraline is described in Japanese Laid-open Patent Publication Showa 48-76852. The combination of these methods gives 1,5-DMN from o-xylene and butadiene.

1,5-DMN belongs to the same group as 2,6-DMN and 1,5-DMN prepared above has the advantage that 2,6-DMN can be prepared from it without having to go through the difficult isomerization between different groups. Various methods have been proposed for the isomerization of 1,5-DMN to prepare 2,6-DMN. As an example of these methods, isomerization in gaseous phase utilizing silica-alumina as a catalyst is described in Japanese Patent Publication Showa 47-50622 and, as another example of them, isomerization in liquid phase utilizing a specific zeolite as a catalyst is described in Japanese Patent Publication Showa 58-004008.

However, in the liquid product obtained by the method described in Japanese Patent Publication Showa 47-50622, considerable amounts of the 2,7-isomer and the 1,7-isomer which belong to a group different from the group of the 2,6-isomer are contained and monomethylnaphthalene and trimethyl-naphthalene which are formed by the disproportionation reaction are also contained in considerable amounts even though the content of the 2,6-isomer is high.

The method described in Japanese Patent Publication Showa 58-004008 produces the 2,6-isomer in low yields even though side reactions, such as the formation of the 2,7-isomer and disproportionation, proceed to a lesser degree.

It is the actual situation at the present time that the 2,6-isomer can not be prepared, by utilizing conventional methods, from the 1,5-isomer in high yields while keeping the side reactions, such as the formation of isomers belonging to groups different from the 2,6-isomer group and disproportionation, to a low level.

When the 2,7-isomer is formed in the process of isomerization to the 2,6-isomer, the yield of the 2,6-isomer is naturally decreased and, furthermore, two component eutectic mixtures of the 2,6-isomer and the 2,7-isomer and three component eutectic mixtures of the 2,6-isomer, the 2,7-isomer and the 1,5-isomer are formed, resulting in the loss of the yield of the 2,6-isomer in the process of the isolation by crystallization after isomerization and in the decrease of purity of the product. Side reactions such as disproportionation reaction also cause a loss of the yield of the 2,6-isomer.

SUMMARY OF THE INVENTION

The present invention has been completed as a result of the extensive investigations undertaken with an object of providing a method for suppressing the formation of isomers belonging to the groups different from the 2,6-isomer group, such as 2,7-isomer, and suppressing side reactions such as disproportionation in the isomerization of 1,5-DMN into 2,6-DMN with a high degree of specific isomerization.

Thus, the method of isomerization of 1,5-DMN into 2,6-DMN in the present invention comprises: the isomerization reaction of 1,5-DMN by utilizing hydrogen fluoride as a catalyst and straight chain saturated aliphatic hydrocarbons having carbon atoms in the range from 5 to 12 as a solvent in a liquid phase at a temperature in the range from 70° to 150° C. (Hydrogen fluoride will be abbreviated as HF in the following descriptions.)

Other and further objects, features and advantages of the present invention will appear more fully from the following description.

DETAILED DESCRIPTION OF THE INVENTION

When DMN's are isomerized in the presence of solid acidic catalysts, such as silica-alumina, zeolite and the like, side reactions easily take place because high temperatures like 250° C. or above are required. It is well known, on the other hand, that DMN's can be isomerized at low temperatures around the room temperature when HF-BF$_3$ is utilized as a catalyst. It is also known that, when HF is utilized alone in the absence of BF$_3$, isomerization to the isomers of the different groups and other side reactions tend to take place because higher temperatures are required.

Isomerization in the presence of HF was investigated by the present inventors, leading to the discovery that, by utilizing a combination of HF and aliphatic saturated hydrocarbons mainly comprising straight chain carbon atoms in the range from 5 to 12 in the absence of BF$_3$, a high degree of isomerization can be attained with a sufficiently high rate at a lower temperature than the reaction utilizing solid acidic catalysts and isomerization to the isomers belonging to the different groups and a side reaction such as disproportionation can be suppressed. It was also discovered that the reaction discovered herein gives better results than that in the presence of HF-BF$_3$.

When the isomerization according to the method of the present invention is performed at a temperature in the range from 70° to 150° C., the concentration of 2,6-DMN in the 2,6-group in the reaction product solution can exceed 50%.

When the isomerization is effected in the presence of silica-alumina, zeolite or the like, the concentration of 2,6-DMN in the 2,6-group in the reaction product solution is 45% at most. When isomerization is effected in the presence of HF-BF$_3$, the corresponding concentration of 2,6-DMN is about 30%. According to the method of the present invention, isomerization to the desired product, 2,6-DMN, can be performed with a high degree of isomerization and the method of the invention gives much more advantageous results than conventional methods.

The amount of HF utilized in the present invention is in the range from 0.5 to 50 moles, preferably from 2 to 30 moles, based on one mole of the DMN's.

When the amount of HF is lower than the amount described above, sufficient mixing of the oil layer and the HF layer becomes difficult and the isomerization can not be performed effectively. When the amount of HF is higher than the amount described above, reaction vessels and the facilities for isolation and purification become too large and the process becomes economically unfavorable.

The isomerization of the DMN's according to the present invention is performed in the system comprising HF and a specific solvent in combination. When the isomerization of DMN is conducted in the presence of HF as a catalyst without utilizing the specific solvent, the rate of the isomerization within the same group of DMN isomers is low, side reactions such as disproportionation and isomerization to DMN's belonging to the different groups take place remarkably and, hence, this condition of isomerization is not favorable for the effective isomerization to 2,6-DMN. It was discovered that, contrary to the above known features, when the isomerization of the DMN's is performed in the presence of HF as a catalyst in combination with the specific solvent, the rate of isomerization within the same group of DMN isomers is increased and side reactions such as disproportionation and isomerization to DMN's belonging to the different groups are suppressed. The present invention was completed on the basis of the discovery.

Solvents generally utilized for dissolving DMN's are aromatic hydrocarbons, such as xylene, toluene, benzene and the like; aliphatic hydrocarbons, such as hexane, heptane and the like; alicyclic hydrocarbons, such as cyclohexane, methylcylcohexane and the like; organic solvents containing oxygen, such as dioxane and the like; and the like other solvents. However, when DMN is isomerized in the presence of HF at a temperature of 70° to 150° C. utilizing a solvent, the formation of undesirable kinds of DMN other than 2,6-DMN, such as 2,7-DMN, 1,7-DMN and the like, and the side reactions, such as disproportionation, can not be suppressed unless the solvent specified in the present invention is utilized.

For example, when an alkyl substituted aromatic hydrocarbon, such as xylene and toluene, or a alicyclic hydrocarbon, such as cyclohexane and methylcyclohexane, is utilized as a solvent, monomethylnaphthalene and trimethylnaphthalene are formed to a remarkable extent and side reactions and isomerization to the DMN's belonging to the different groups can not be suppressed. When benzene is utilized as a solvent, side reactions and the isomerization to the DMN's belonging to different groups are not remarkable at the temperatures below 100° C. but become more remarkable at the temperatures above 100° C. When an organic solvent containing oxygen, such as dioxane, is utilized as a solvent, the solvent is likely to be decomposed through the dehydration reaction with HF and can not be favorably utilized in the reaction.

When the solvent comprising saturated aliphatic hydrocarbons of mainly straight chain having carbon atoms in the range from 5 to 12 is utilized according to the method of the present invention, side reactions such as disproportionation and isomerization to DMN's belonging to the different groups are suppressed, the rate of isomerization within the same group is enhanced and a high degree of isomerization to 2,6-DMN in a short period of time can be attained.

When branched aliphatic hydrocarbons are singly utilized as a solvent, just like the reaction under utilizing xylene or cyclohexane as a solvent, monomethylnaphthalene and trimethylnaphthlalaene are formed to a remarkable extent and side reactions and isomerization to DMN's belonging to the different groups can not be suppressed. On the other hand, when the saturated aliphatic hydrocarbons of mainly straight chain having carbon atoms in the range from 5 to 12 are singly utilized as a solvent, side reactions such as disproportionation are suppressed and the formation of by-products is very slight. The remarkable result that isomerization to DMN's belonging to the different groups is totally suppressed and that the formation of the 2,7-isomer and the 1,7-isomer is not detected can be confirmed in this case. When the solvent comprises the straight chain saturated aliphatic hydrocarbons having carbon atoms in the range from 5 to 12 as a major component and the branched saturated aliphatic hydrocarbons having carbon atoms in the range from 5 to 12 as a minor component, the rate of isomerization of DMN's is found to be increased further while the side reactions rarely take place. However, when the content of the branched saturated aliphatic hydrocarbon is increased, monomethylnaphthalene and trimethylnaphthalene as well as the isomers other than those belonging to the 2,6-isomer group such as 2,7-DMN and 1,7-DMN are more easily formed.

The effect of the concentration of the branched saturated aliphatic hydrocarbons was further investigated for the purpose of suppressing the formation of by-products, such as monomethylnaphthalene and trimethylnaphthalene, and isomers other than the isomers of the 2,6-group and also for the purpose of increasing the rate of the isomerization reaction and the following feature was discovered. When the concentration of the branched saturated aliphatic hydrocarbons in the saturated aliphatic hydrocarbon solvent is 20% or less, preferably 10% or less, side reactions such as disproportionation rarely take place and only very slight amount of by-products are formed. The isomerization to the isomers belonging to the different groups does not take place at all and neither the 2,7-isomer nor the 1,7-isomer is detected in the product. The rate of isomerization is high and the time required to reach the equilibrium is short. The present invention was also completed on the basis of the above discovery.

The amount of the solvent utilized in the invention to fully make use of the advantage of the present invention is in the range from 0.2 to 20 weight parts, preferably from 1 to 10 weight parts, based on one weight part of the DMN's. When the solvent is utilized within the range described herein, side reactions such as disproportionation and the isomerization to the isomers belonging to the different groups can be suppressed and a high degree of isomerization to the 2,6-isomer can be attained in a short period of time. Utilizing the solvent in the range described herein is also favorable for processability in the isomerization process, in the extraction process of DMN from the HF layer and in the crystallization process.

When the amount of the solvent utilized is larger than the range described above, the amount of DMN extracted from the HF layer tends to be increased but the energy consumption necessary for mixing and for the isolation of DMN from the solvent becomes increased and the condition is not favorable. When the amount of the solvent utilized is smaller than the range described above, the condition is not favorable because side reactions such as disproportionation and the isomerization to the isomers belonging to the different groups are increased, extraction of DMN from the HF layer becomes insufficient, processability in the crystallization process becomes inferior and the purity of 2,6-DMN prepared is decreased.

By utilizing the solvent of the present invention in an amount described above, isomerization to the isomers belonging to the different groups and side reactions such as disproportionation can be suppressed, a high degree of the isomerization to the 2,6-isomer can be attained in a short period of time and an industrial isomerization having an excellent processability can be constructed.

The melting points of 2,6-DMN, 1,6-DMN and 1,5-DMN are 112° C., −16° C. and 82° C., respectively. When a mixture of these DMN isomers is utilized as the starting material for the reaction, the mixture is in a liquid state at the temperature of the reaction in the present invention and a solvent is not necessarily utilized as long as only the isomerization in the presence of HF is concerned. When the isomerization of DMN is conducted in the presence of HF alone without utilizing the solvent in the present invention, the reaction product solution can be easily separated into an oil layer and a HF layer. A part of DMN is contained in the HF layer as well as in the oil layer, and the amount in the HF layer is greater than that with the use of a solvent.

As a general practice of the process operation, the two layers are first separated from each other, then the oil layer is sent to the process for isolation 2,6-DMN and the HF layer is sent to the isomerization process for recycling.

Since a considerable amount of DMN is dissolved in the HF layer sent for recycling, the reactions proceeds further and isomerization to the isomers other than those of the 2,6-group and side reactions such as disproportionation take place. It is therefore necessary that the amount of DMN in the HF layer sent for recycling is kept as small as possible.

When the solvent of the present invention is utilized in the isomerization process, most of DMN in the HF layer be extracted to the oil layer and the amount of DMN remained in the HF layer can be kept very small.

From the reaction product of the isomerization process separated in the oil layer, the desired product, 2,6-DMN, is isolated usually by crystallization and the remaining solution containing a rich amount of the 1,6-isomer and the 1,5-isomer is sent to the isomerization process for recycling. When the solvent of the invention is utilized, the crystallized 2,6-DMN can be efficiently separated from the remaining solution and efficient operation is realized in the crystallization process.

Thus, due to the isomerization of DMN's with the utilization of HF and the specific solvent in combination, the reaction product solution containing the solvent can be directly sent to the crystallization process. Of course, a part of the solvent can be driven off if necessary before the isomerization product solution is sent to the crystallization. Therefore, with the use of the solvent in the present invention, the operation of the both processes becomes easier, the yield and the purity of 2,6-DMN is increased to a large extent and the excellent process for the industrial production of 2,6-DMN can be constructed.

The isomerization reaction in the method of the present invention is performed at a temperature in the range from 70° to 150° C., preferably in the range from 80° to 120° C.

When the temperature is higher than that described above, side reactions such as the decomposition of DMN and vigorous polymerization take place and, when the temperature is lower than that described above, the rate of the isomerization reaction becomes decreased. Thus, temperatures outside of the range described above are not favorable.

As described in the above in detail, when DMN's are isomerized according to the method of the present invention, side reactions and isomerization to the isomers belonging to the different groups can be suppressed and 2,6-DMN can be obtained with a high degree of isomerization in a short period of time.

The isomerization reaction according to the method of the present invention is performed in a liquid phase. Because the boiling point of HF at the atmospheric pressure is 20° C., the reaction is performed under pressure. The type of reaction process is not particularly limited so long as the oil layer and the HF layer are sufficiently mixed together and any of batch types, semi-continuous types and continuous flow types may be utilized.

DESCRIPTION OF THE PREFERRED EMBODIMENTS

The present invention will be understood more readily with reference to the following examples; however these examples are intended to illustrate the invention and are not to be construed to limit the scope of the invention.

Examples 1, 2, 3 and 4

Into an autoclave of the inner volume of 300 ml made of Hastelloy C and equipped with a magnetic driven stirrer, 50 g of 1,5-DMN, 70 g of straight chain aliphatic hydrocarbon solvent and 100 g of anhydrous HF were charged. After the reaction vessel was closed tightly, the mixture was heated to a designated temperature while it was stirred and kept at the temperature for a designated time under stirring. After the reaction was finished, the reaction mixture was taken out from the reaction vessel and analyzed and the result of the reaction was evaluated. The solvent utilized, the reaction temperature, the reaction time and the result of the evaluation of each Example are listed in Table 1. In the evaluation of the result of the reaction in Table 1, the amount (weight %) of the products having boiling points lower than the DMN (including mono-methylnaphthalene and naphthalene), the amount (weight %) of the products having boiling points higher than the DMN (including trimethylnaphthalene), both formed from the DMN, the amount (weight %) of the recovered DMN and the composition of isomers (weight %) in the recovered DMN are listed.

Examples 5, 6 and 7

Isomerization reaction was conducted in the same way as in Example 1 except that the straight chain aliphatic hydrocarbon containing branched chain saturated aliphatic hydrocarbon is utilized as a solvent. The solvent utilized, the reaction temperature, the reaction time and the result of the evaluation of each Example are listed in Table 1. Addition of a small amount of the branched chain saturated aliphatic hydrocarbon increased the rate of isomerization.

Example 8

Isomerization reaction was conducted in the same way as in Example 5 except that the temperature of the reaction was 120° C. and the time of the reaction was 30 minutes. Results are shown in Table 1.

Example 9

Isomerization reaction was conducted in the same way as in Example 5 except that 50 g of a mixture of DMN isomers containing 25% of 1,5-DMN, 54% of 1,6-DMN and 21% of 2,6-DMN was utilized as a starting material in place of 50 g of 1,5-DMN. Results are shown in Table 1.

Example 10

Isomerization reaction was conducted in the same way as in Example 7 except that 60 g of HF was utilized in place of 100 g of HF. Results are shown in Table 1.

TABLE 1

| Example | 1 | 2 | 3 | 4 | 5 | 6 | 7 | 8 | 9 | 10 |
|---|---|---|---|---|---|---|---|---|---|---|
| solvent | n-heptane 100% | n-heptane 100% | n-decane 100% | n-pentane 100% | n-heptane 95% 2-methylhexane 5% | n-heptane 85% 2-methylhexane 15% | n-dodecane 95% isoctane 5% | n-heptane 95% 2-methylhexane 5% | n-heptane 95% 2-methylhexane 5% | n-dodecane 95% isoctane 5% |
| reaction temperature (°C.) | 90 | 90 | 80 | 100 | 90 | 90 | 90 | 120 | 90 | 90 |
| reaction time (min) | 75 | 120 | 180 | 60 | 75 | 75 | 75 | 30 | 75 | 75 |
| low boiling point component (%) | 0.17 | 0.25 | 0.14 | 0.15 | 0.32 | 0.72 | 0.28 | 0.74 | 0.44 | 0.30 |
| high boiling point component (%) | 0.21 | 0.41 | 0.20 | 0.64 | 0.13 | 0.81 | 0.20 | 1.13 | 0.21 | 0.17 |
| DMN total (%) | 99.62 | 99.34 | 99.66 | 98.85 | 99.55 | 98.47 | 99.52 | 98.13 | 99.35 | 99.53 |
| 2,6-DMN | 38.7 | 52.4 | 51.8 | 52.0 | 51.8 | 52.3 | 52.0 | 52.7 | 53.0 | 51.1 |
| 1,6-DMN | 41.3 | 40.8 | 41.0 | 40.6 | 41.0 | 40.7 | 40.2 | 40.1 | 40.5 | 40.8 |
| 1,5-DMN | 20.0 | 6.8 | 7.2 | 7.4 | 7.2 | 7.0 | 7.8 | 7.2 | 6.5 | 8.1 |
| 2,7-DMN | 0 | 0 | 0 | 0 | 0 | 0 | 0 | 0 | 0 | 0 |
| 1,7-DMN | 0 | 0 | 0 | 0 | 0 | 0 | 0 | 0 | 0 | 0 |

Comparative examples 1, 2, 3, and 4

Isomerization reaction was conducted in the same way as in Example 1 except that, in Comparative example 1, toluene; in Comparative example 2, cyclohexane; in Comparative example 3, 2-methylhexane; and in Comparative example 4, n-heptane containing 50 weight % of 2-methylhexane were utilized as a solvent. Results are shown in Table 2. The concentration of 2,6-DMN is lower than Example 1 and side reactions such as disproportionation and the isomerization to the isomers belonging to the groups other than the 2,6-group were observed to a remarkable degree. It is shown that the reactions under these conditions lead to very unsatisfactory results.

Comparative examples 5 and 6

Isomerization reaction was conducted in the same way as in Example 1 except that benzene was utilized as a solvent and the reaction was conducted for 2 hours in Comparative example 5 and for 3 hours in Comparative example 6. The results are shown in Table 2. The rate of isomerization was low and the reactions in these conditions lead to unsatisfactory results.

Comparative example 7

Isomerization reaction was conducted in the same way as in Example 1 except that benzene was utilized as a solvent and the reaction was conducted for 1 hour at 120° C. The results are shown in Table 2. Side reactions such as disproportionation and the isomerization to the isomers belonging to the groups other than the 2,6- group were observed to a remarkable degree. It is shown that the reaction under these conditions leads to very unsatisfactory results.

Comparative example 8

Isomerization reaction was conducted in the same way as in Example 1 except that no solvent was utilized. The results are shown in Table 2. The concentration of 2,6-DMN is lower than Example 1 and side reactions such as disproportionation and the isomerization to the isomers belonging to the groups other than the 2,6- group were observed to a remarkable degree. It is shown that the reaction under these conditions leads to very unsatisfactory results.

Comparative example 9

Isomerization reaction was conducted in the same way as in Example 1 except that 24 g of $BF_3$ was added and the reaction was conducted for 3 hours at 40° C. The results are shown in Table 2. The concentration of 2,6-DMN is lower than that of Example 1. It is shown that the reaction under these conditions leads to unsatisfactory results. When the reaction time was extended to 6 hours, no improvement in the concentration of 2,6-DMN was found.

TABLE 2

| Comparative Example | 1 | 2 | 3 | 4 | 5 | 6 | 7 | 8 | 9 |
|---|---|---|---|---|---|---|---|---|---|
| solvent | toluene | cyclo-hexane | 2-methyl-hexane | n-heptane 50% 2-methyl-hexane 50% | benzene | benzene | benzene | none | n-heptane HF-$BF_3$ |
| reaction temperature (°C.) | 90 | 90 | 90 | 90 | 90 | 90 | 120 | 90 | 40 |
| reaction time (min) | 75 | 75 | 75 | 75 | 120 | 180 | 60 | 75 | 180 |
| low boiling point component (%) | 5.38 | 4.18 | 8.65 | 4.1 | 0.41 | 0.72 | 3.49 | 7.54 | 0.42 |
| high boiling point component (%) | 7.15 | 6.72 | 13.43 | 10.7 | 0.38 | 0.88 | 6.43 | 9.81 | 2.24 |
| DMN total (%) | 87.47 | 89.10 | 77.92 | 85.2 | 99.21 | 98.40 | 90.18 | 82.65 | 97.34 |
| 2,6-DMN | 23.3 | 31.6 | 28.4 | 40.1 | 44.5 | 52.4 | 38.9 | 14.8 | 30.5 |
| 1,6-DMN | 36.1 | 38.9 | 38.0 | 40.7 | 35.9 | 40.6 | 39.0 | 33.5 | 65.7 |
| 1,5-DMN | 37.2 | 26.7 | 28.7 | 16.0 | 19.6 | 7.0 | 19.2 | 39.7 | 3.8 |
| 2,7-DMN | 1.9 | 1.2 | 3.1 | 2.0 | 0 | 0 | 1.8 | 7.8 | 0 |
| 1,7-DMN | 1.5 | 1.6 | 1.8 | 1.2 | 0 | 0 | 1.1 | 4.2 | 0 |

While the present invention has been particularly shown and described with reference to preferred embodiments thereof, it will be understood by those skilled in the art that the foregoing and other changes in form and details can be made therein without departing from the spirit and scope of the invention.

To summarize the advantages obtained by the present invention, isomerization to the isomers belonging to the different groups such as 2,7-DMN and side reactions such as disproportionation are suppressed in the isomerization of DMN's and a very high degree of the isomerization to 2,6-DMN can be attained. Thus, the method of the present invention is highly valuable as an industrial process.

What is claimed is:

1. A method of isomerization of dimethylnaphthalenes to 2,6-dimethylnaphthalene which comprises heating in a pressured vessel a mixture of dimethylnaphthalenes in a liquid phase comprising a solvent consisting essentially of a straight chain saturated aliphatic hydrocarbon having 5 to 12 carbon atoms at a temperature of from 70° to 150° C. in the presence of a catalyst consisting essentially of hydrogen fluoride.

2. The method of isomerization of dimethylnaphthalenes to 2,6-dimethylnaphthalene as claimed in claim 1 wherein said straight chain saturated aliphatic hydrocarbon solvent contains 20% or less of branched chain saturated aliphatic hydrocarbons having 5 to 12 carbon atoms.

3. The method of isomerization of dimethylnaphthalenes to 2,6-dimethylnaphthalene as claimed in claim 1 wherein said straight chain saturated aliphatic hydrocarbon solvent contains 10% or less of branched chain saturated aliphatic hydrocarbons having 5 to 12 carbon atoms.

4. The method of isomerization of dimethylnaphthalenes to 2,6-dimethylnaphthalene as claimed in claim 1 wherein said straight chain saturated aliphatic hydrocarbon solvent is a compound selected from the group consisting of n-pentane, n-hexane, n-heptane, n-octane, n-nonane, n-decane, n-undecane and n-dodecane.

5. The method of isomerization of dimethylnaphthalenes to 2,6-dimethylnaphthalene as claimed in claim 1 wherein the amount of said straight chain saturated aliphatic hydrocarbon solvent is from 0.2 to 20 weight parts based on one weight part of the dimethylnaphthalenes.

6. The method of isomerization of dimethylnaphthalenes to 2,6-dimethylnaphthalene as claimed in claim 1 wherein the amount of said straight chain saturated aliphatic hydrocarbon solvent is from 1 to 10 weight parts based on one weight part of the dimethylnaphthalenes.

7. The method of isomerization of dimethylnaphthalenes to 2,6-dimethylnaphthalene as claimed in claim 1 wherein the amount of hydrogen fluoride is from 0.5 to 50 moles based on one mole of the dimethylnaphthalenes.

8. The method of isomerization of dimethylnaphthalenes to 2,6-dimethylnaphthalene as claimed in claim 1 wherein the amount of hydrogen fluoride is from 2 to 30 moles based on one mole of the dimethylnaphthalenes.

9. The method of isomerization of dimethylnaphthalenes to 2,6-dimethylnaphthalene as claimed in claim 1 wherein said heating is at a temperature of from 80° to 120° C.

10. The method of isomerization of dimethylnaphthalenes to 2,6-dimethylnaphthalene as claimed in claim 4 wherein
said straight chain saturated aliphatic hydrocarbon contains 20% or less of a branched chain saturated aliphatic hydrocarbon having 5 to 12 carbon atoms;
the amount of said straight chain saturated aliphatic hydrocarbon solvent is from 0.2 to 20 weight parts based on one weight part of the dimethylnaphthalenes; and
the amount of hydrogen fluoride is from 0.5 to 50 moles based on one mole of the dimethylnaphthalenes.

11. The method of isomerization of dimethylnaphthalenes to 2,6-dimethylnaphthalene as claimed in claim 4 wherein
said straight chain saturated aliphatic hydrocarbon solvent comprises 10% or less of branched chain saturated aliphatic hydrocarbons having 5 to 12 carbon atoms;
the amount of said straight chain saturated aliphatic hydrocarbon solvent is from 1 to 10 weight parts based on one weight part of the dimethylnaphthalenes; and
the amount of hydrogen fluoride is from 2 to 30 moles based on one mole of the dimethylnaphthalenes.

12. The method of isomerization of dimethylnaphthalenes to 2,6-dimethylnaphthalene as claimed in claim 10 wherein said branched chain hydrocarbon is selected from the group consisting of branched pentane, hexane, heptane, octane, nonane, decane, undecane and dodecane.

13. The method of isomerization of dimethylnaphthalenes to 2,6-dimethylnaphthalene as claimed in claim 11 wherein said branched chain hydrocarbon is selected from the group consisting of branched pentane, hexane, heptane, octane, nonane, decane, undecane and dodecane.

14. The method of isomerization of dimethylnaphthalenes to 2,6-dimethylnaphthalene as claimed in claim 10 wherein said heating is at a temperature of from 80° to 120° C.

15. The method of isomerization of dimethylnaphthalenes to 2,6-dimethylnaphthalene as claimed in claim 11 wherein said heating is at a temperature of from 80° to 120° C.

16. The method of isomerization of dimethylnaphthalenes to 2,6-dimethylnaphthalene as claimed in claim 12 wherein said heating is at a temperature of from 80° to 120° C.

17. The method of isomerization of dimethylnaphthalenes to 2,6-dimethylnaphthalene as claimed in claim 13 wherein said heating is at a temperature of from 80° to 120° C.

* * * * *